United States Patent
Dietiker

(10) Patent No.: US 7,124,048 B2
(45) Date of Patent: Oct. 17, 2006

(54) SYSTEM AND METHOD FOR A SELF-CALIBRATING NON-INVASIVE SENSOR

(75) Inventor: Thomas Dietiker, Rancho Palos Verdes, CA (US)

(73) Assignee: Elekon Industries USA, Inc., Torrance, CA (US)

( * ) Notice: Subject to any disclaimer, the term of this patent is extended or adjusted under 35 U.S.C. 154(b) by 41 days.

(21) Appl. No.: 11/007,656

(22) Filed: Dec. 8, 2004

(65) Prior Publication Data

US 2006/0122801 A1 Jun. 8, 2006

Related U.S. Application Data

(63) Continuation of application No. 10/149,779, filed on Jun. 12, 2002, now Pat. No. 6,889,153, which is a continuation of application No. PCT/US01/25109, filed on Aug. 9, 2001.

(60) Provisional application No. 60/225,021, filed on Aug. 11, 2001.

(51) Int. Cl.
G01D 18/00 (2006.01)

(52) U.S. Cl. .................. 702/104; 702/85; 356/40; 600/310; 600/331; 600/473; 600/476

(58) Field of Classification Search ............. 702/104, 702/85, 196; 356/40; 600/320, 328, 323, 600/473, 476, 310, 331
See application file for complete search history.

(56) References Cited

U.S. PATENT DOCUMENTS

| | | | |
|---|---|---|---|
| 3,638,640 A | 2/1972 | Shaw | |
| 3,799,672 A | 3/1974 | Vurek | |
| 3,998,550 A | 12/1976 | Konishi et al. | |
| 4,603,700 A | 8/1986 | Nichols et al. | |
| 4,621,643 A | 11/1986 | New, Jr. et al. | |
| 4,653,498 A | 3/1987 | New, Jr. et al. | |
| 4,700,708 A | 10/1987 | New, Jr. et al. | |
| 4,714,080 A | 12/1987 | Edgar, Jr. et al. | |
| 4,770,179 A | 9/1988 | New, Jr. et al. | |
| 4,796,636 A | 1/1989 | Branstetter et al. | |
| 4,824,242 A | 4/1989 | Frick et al. | |
| 4,834,532 A | 5/1989 | Yount | |
| 4,867,557 A | 9/1989 | Takatani et al. | |
| 4,869,253 A | 9/1989 | Craig, Jr. et al. | |
| 4,913,150 A | 4/1990 | Cheung et al. | |
| 4,942,877 A | 7/1990 | Sakai et al. | |
| 5,058,588 A | 10/1991 | Kaestle | |
| 5,111,817 A | 5/1992 | Clark et al. | |
| 5,190,038 A | 3/1993 | Polson et al. | |
| 5,216,598 A | 6/1993 | Branstetter et al. | |
| 5,218,962 A | 6/1993 | Mannheimer et al. | |
| 5,246,002 A | 9/1993 | Prosser | |

(Continued)

FOREIGN PATENT DOCUMENTS

EP 0 898 932 A1 3/1999

(Continued)

OTHER PUBLICATIONS

PCT International Search Report; Dated Feb. 27, 2002.

*Primary Examiner*—John Barlow
*Assistant Examiner*—Hien Vo
(74) *Attorney, Agent, or Firm*—Factor & Lake

(57) ABSTRACT

A non-invasive emitter-photodiode sensor which is able to provide a data-stream corresponding to the actual wavelength of light emitted thereby allowing calibration of the sensor signal processing equipment and resulting in accurate measurements over a wider variation in emitter wavelength ranges.

20 Claims, 13 Drawing Sheets

U.S. PATENT DOCUMENTS

| | | |
|---|---|---|
| 5,259,381 A | 11/1993 | Cheung et al. |
| 5,267,562 A | 12/1993 | Ukawa et al. |
| 5,278,627 A | 1/1994 | Aoyagi et al. |
| 5,279,295 A | 1/1994 | Martens et al. |
| 5,368,224 A | 11/1994 | Richardson et al. |
| 5,377,674 A | 1/1995 | Kuestner |
| 5,398,680 A | 3/1995 | Polson et al. |
| 5,421,329 A | 6/1995 | Casciani et al. |
| 5,448,991 A | 9/1995 | Polson et al. |
| 5,490,505 A | 2/1996 | Diab et al. |
| 5,503,148 A | 4/1996 | Pologe et al. |
| 5,564,417 A | 10/1996 | Chance |
| 5,632,272 A | 5/1997 | Diab et al. |
| 5,645,059 A | 7/1997 | Fein et al. |
| 5,685,299 A | 11/1997 | Diab et al. |
| 5,692,505 A | 12/1997 | Fouts |
| 5,694,930 A | 12/1997 | Pries et al. |
| 5,758,644 A | 6/1998 | Diab et al. |
| 5,779,630 A | 7/1998 | Fein et al. |
| 5,782,756 A | 7/1998 | Mannheimer |
| 5,807,247 A | 9/1998 | Merchant et al. |
| 5,820,550 A | 10/1998 | Polson et al. |
| 5,823,950 A | 10/1998 | Diab et al. |
| 5,827,182 A | 10/1998 | Raley et al. |
| 5,830,137 A | 11/1998 | Scharf |
| 5,841,536 A | 11/1998 | Dimmick |
| 5,842,981 A | 12/1998 | Larsen et al. |
| 5,921,921 A | 7/1999 | Potratz et al. |
| 5,934,277 A | 8/1999 | Mortz |
| 5,987,343 A | 11/1999 | Kinast |
| 5,995,858 A | 11/1999 | Kinast |
| 6,011,986 A | 1/2000 | Diab et al. |
| 6,018,673 A | 1/2000 | Chin et al. |
| 6,036,642 A | 3/2000 | Diab et al. |
| 6,041,247 A | 3/2000 | Weckstrom et al. |
| 6,044,283 A | 3/2000 | Fein et al. |
| 6,081,735 A | 6/2000 | Diab et al. |
| 6,115,621 A | 9/2000 | Chin |
| 6,163,715 A | 12/2000 | Larsen et al. |
| 6,181,959 B1 | 1/2001 | Schollermann et al. |
| 6,206,830 B1 | 3/2001 | Diab et al. |
| 6,215,295 B1 | 4/2001 | Smith, III |
| 6,226,540 B1 | 5/2001 | Bernreuter |
| 6,230,035 B1 | 5/2001 | Aoyagi et al. |
| 6,253,097 B1 | 6/2001 | Aronow et al. |
| 6,263,222 B1 | 7/2001 | Diab et al. |
| 6,272,363 B1 | 8/2001 | Casciani et al. |
| 6,356,774 B1 | 3/2002 | Bernstein et al. |
| 6,501,974 B1 | 12/2002 | Huiku |
| 6,537,225 B1 | 3/2003 | Mills |
| 6,600,940 B1 | 7/2003 | Fein et al. |
| 6,611,320 B1 * | 8/2003 | Lindberg et al. .............. 356/40 |
| 6,628,975 B1 | 9/2003 | Fein et al. |
| 6,667,803 B1 | 12/2003 | Flessland et al. |
| 6,673,596 B1 | 1/2004 | Sayler et al. |
| 2001/0005773 A1 | 6/2001 | Larsen et al. |
| 2001/0020123 A1 | 9/2001 | Diab et al. |
| 2001/0029326 A1 | 10/2001 | Diab et al. |
| 2001/0037059 A1 | 11/2001 | Stone et al. |
| 2002/0161287 A1 | 10/2002 | Schmitt |

FOREIGN PATENT DOCUMENTS

| | | |
|---|---|---|
| EP | 0945 100 A1 | 9/1999 |
| EP | 0992 214 A2 | 4/2000 |
| WO | WO 02/14793 A2 | 2/2002 |

\* cited by examiner

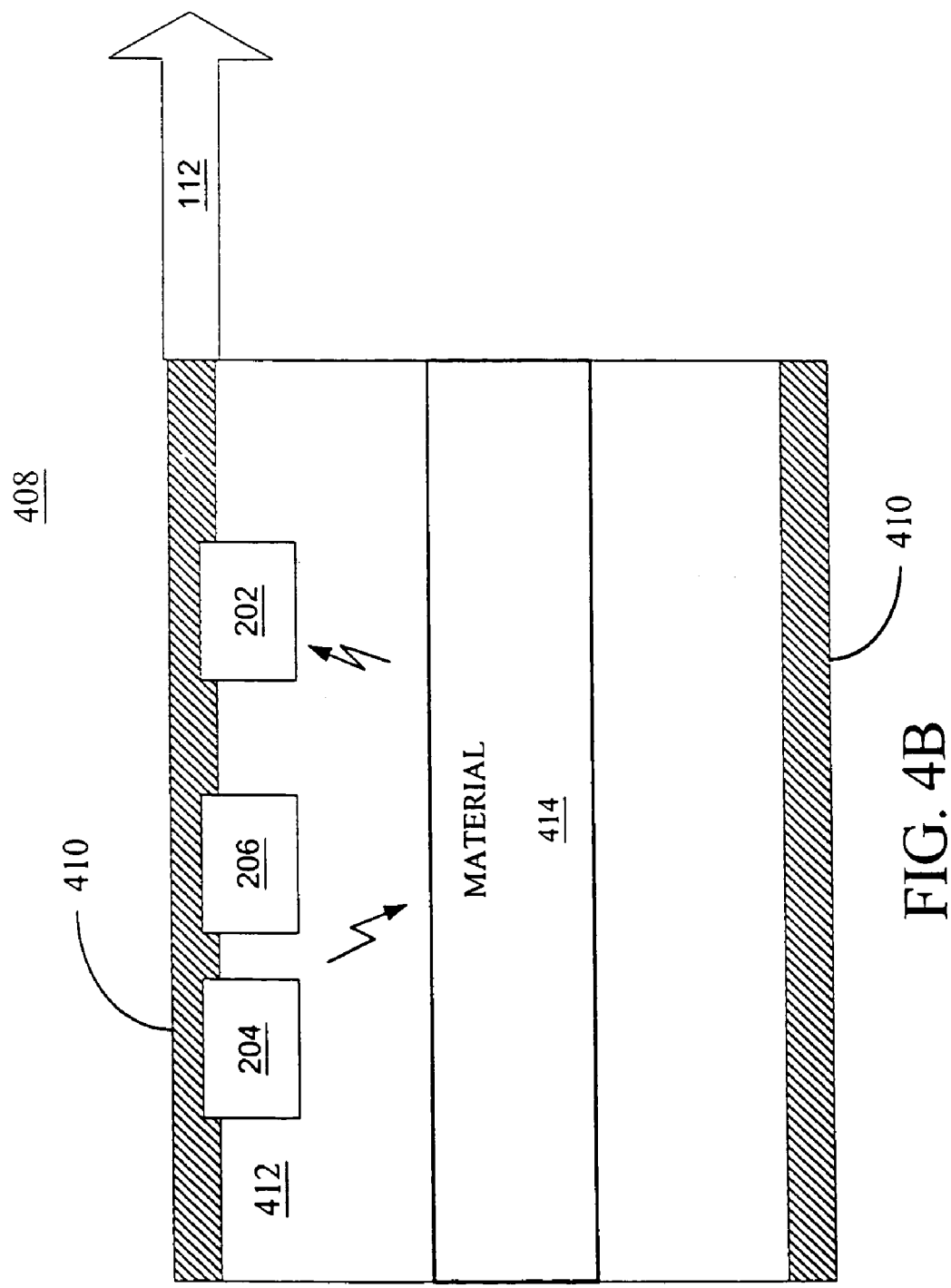

US 7,124,048 B2

SYSTEM AND METHOD FOR A SELF-CALIBRATING NON-INVASIVE SENSOR

CROSS-REFERENCE TO RELATED APPLICATIONS

This application is a continuation of U.S. patent application Ser. No. 10/149,779, filed Jun. 12, 2002 now U.S. Pat. No. 6,889,153, and entitled System and Method For A Self-Calibrating Non-Invasive Sensor, which is a continuation of International Application No., PCT/US01/25109, filed Aug. 9, 2001, and entitled System and Method For A Self-Calibrating Non-Invasive Sensor, which claims the benefit of U.S. Provisional Patent Application No. 60/225,021, filed on Aug. 11, 2001, and entitled Self Calibrating Non-Invasive Blood Component Sensor.

BACKGROUND OF THE INVENTION

1. Technical Field

This invention relates generally to non-invasive sensing devices, and in particularly to calibrating these non-invasive sensing devices.

2. Related Art

Coherent light sources are utilized in a broad range of applications in many distinct fields of technology including the consumer, industrial, medical, defense and scientific fields. In the medical field an emitter-receiver pair of coherent light sources in form of light-emitting diodes (LEDs) are often utilized in medical sensing devices to obtain accurate non-invasive measurements. An example application of such a medical sensing device may include a blood constituent monitoring system and/or a non-invasive oximeter that may be utilized to monitor arterial oxygen saturation.

In non-invasive oximetry, coherent light having a known specific wavelength is typically transmitted from an emitter LED through a target, such as biological tissue carrying blood, to a photodetector. The photodetector receives and measures a portion of transmitted coherent light that is neither absorbed nor reflected from the blood in the biological tissue in order to determine the oxygen saturation (SP02) within the blood. Similarly, an example of an industrial application may include a non-invasive sensor system having a coherent light of a known specific wavelength transmitted from a coherent light source (such as an LED emitter) through a target, such as a fluid or material, to photodetector.

Unfortunately, these types of non-invasive sensor systems utilizing a coherent light source require accurate prior knowledge of the wavelength of the coherent light source in order to determine the amount of coherent light that is absorbed or reflected through the target. One way of having the prior knowledge of the wavelength is to select coherent light source emitters that have wavelengths within a certain range of tolerance. As such, attempts at determining the wavelength have included a binning process of selecting LEDs within the required nominal wavelength specifications.

However, it is appreciated by those skilled in the art and familiar with the production of emitter-photodiode sensing devices that there is a need to be able to select from a wider variation of emitter output wavelengths in reducing the production costs and defect rates of the sensing devices. As an example, typical production techniques require selection of an emitter within 2 nm of a target wavelength, which may lead to rejection of 40–60% of the component emitters. Moreover, an additional problem is that a selected emitter, which was within the target wavelength at time of production, will typically degrade over time, vary with temperature, and the drive circuit may become unstable and cause a wavelength shift.

Attempts to solve the wavelength shift problem have included systems that correlate the wavelength shift to a change in drive circuit current. The change in drive circuit current drives the LED to a specific wavelength. Typically, these systems include a scheme for determining the wavelength shift of the photodiodes via a series of filters, diffusers and a plurality of photodetectors. Unfortunately, this approach is too complex and expensive for practical manufacturing techniques.

Therefore, there is a need for a non-invasive sensor system that is capable of measuring the wavelength of a light source without requiring prior knowledge of the wavelength of the light source and is not complex or expensive to manufacture.

SUMMARY

This invention is a self-calibrating sensor system "SCSS" capable of determining the actual wavelength of light emitted from a light source resulting in accurate measurements over a wide variation of wavelength ranges. In an example operation, the SCSS is capable of receiving incident light radiation from the at least one light source at a sensor probe and producing a calibrated signal corresponding to the received incident light radiation at the sensor probe.

As an example implementation of the SCSS architecture, the SCSS may include a sensor probe receiving incident light radiation from at least one light source and a calibration circuit in signal communication with the sensor probe. The calibration circuit may produce a calibrated signal corresponding to the received incident light radiation at the sensor probe. The sensor probe may include a wavelength sensor. The wavelength sensor may include a first diode configured to receive short wavelengths from the incident light radiation and produce a first photocurrent signal and a second diode configured to receive long wavelengths from the incident light radiation and produce a second photocurrent signal.

BRIEF DESCRIPTION OF THE FIGURES

The invention may be better understood with reference to the following figures. The components in the figures are not necessarily to scale, emphasis instead being placed upon clearly illustrating the principles of the invention. Moreover, in the figures, like reference numerals designate corresponding parts throughout the several views.

FIG. 4B illustrates a cross-sectional view of example reflective implementation of the probe shown in FIG. 2.

DETAILED DESCRIPTION OF THE PREFERRED EMBODIMENT

Figure 1:
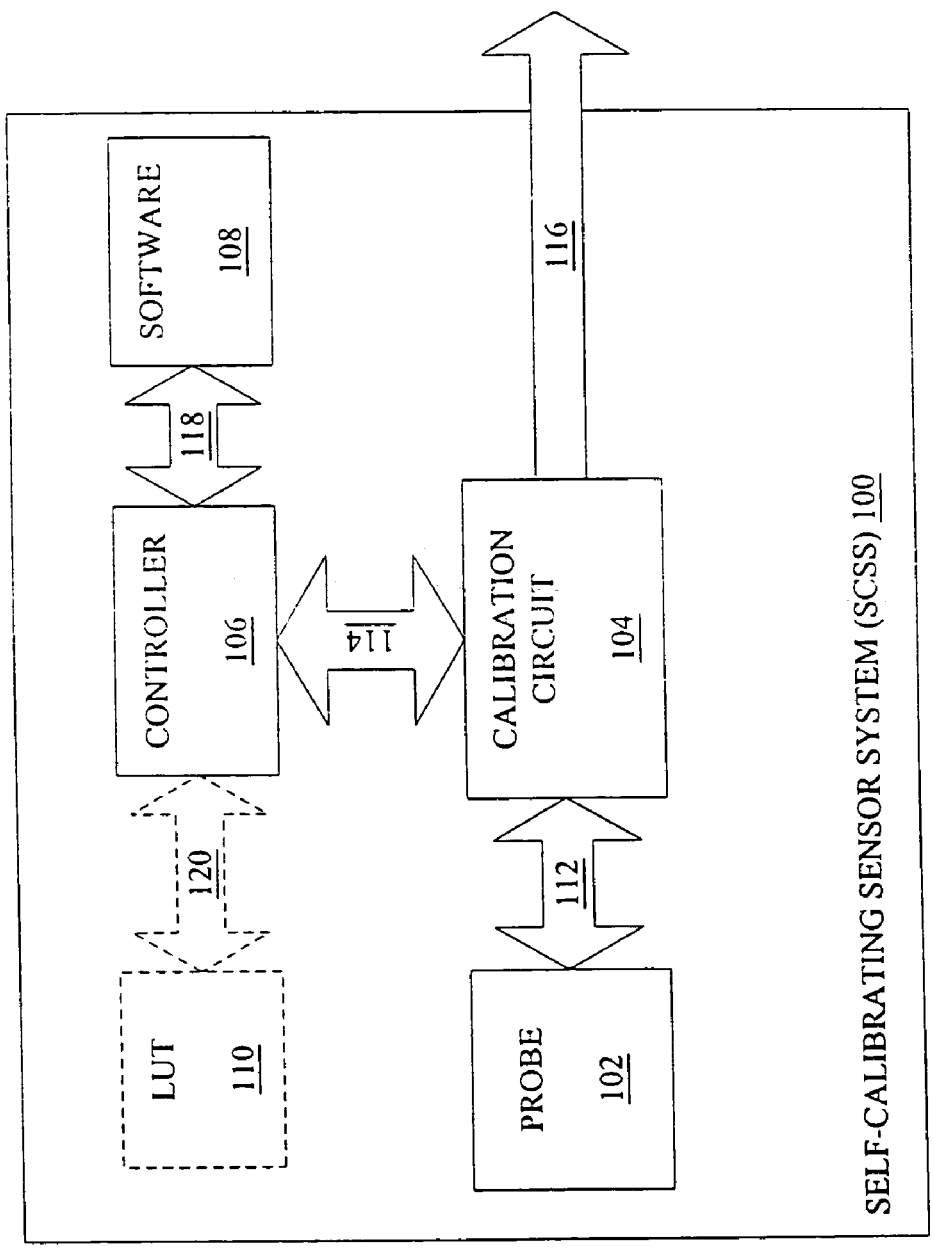
FIG. 1 illustrates a block diagram of an example implementation of a self-calibrating sensor system (SCSS).

FIG. 1 illustrates a block diagram of a self-calibrating sensor system (SCSS) 100. The SCSS 100 may include a probe 102, a calibration circuit 104, a controller 106, software 108 located on in memory (not shown) and optional lookup table ("LUT") 110. The probe 102 is in signal communication, via signal path 112, to the calibration circuit 104. The calibration circuit 106 may be a divider and/or comparator circuit.

The calibration circuit 104 is in signal communication to the controller 106 and an external output device (not shown) via signal paths 114 and 116, respectively. The controller 106 is in signal communication to software 108 and optional LUT 110 via signal paths 118 and 120, respectively.

The controller 106 may be any general-purpose processor such as an Intel XXX86, Motorola 68XXX or PowerPC, DEC Alpha or other equivalent processor. Alternatively, a specific circuit or oriented device may selectively be utilized as the controller 106. Additionally, the controller 106 may also be integrated into a signal semiconductor chip such as an Application Specific Integrated Chip (ASIC) or Reduced Instruction Set Computer (RISC), or may be implemented via a Digital Signal Processor (DSP) chip. Examples of a specific circuit or oriented device for the controller 106 may also be a mixed sionac ASIC.

The software 108 may be resident in memory (not shown) located either internally or externally to the controller 106. The software 108 includes both logic enabling the controller 106 to operate and also logic for self-calibrating the SCSS 100.

An example of the external output device may be an oximeter such as a NPB40 manufactured by Nellcor of Pleasanton, Calif., a 9840 Series pulse oximeter manufactured by Nonin Medical, Inc. of Plymouth, Minn., or an equivalent device.

Figure 2:
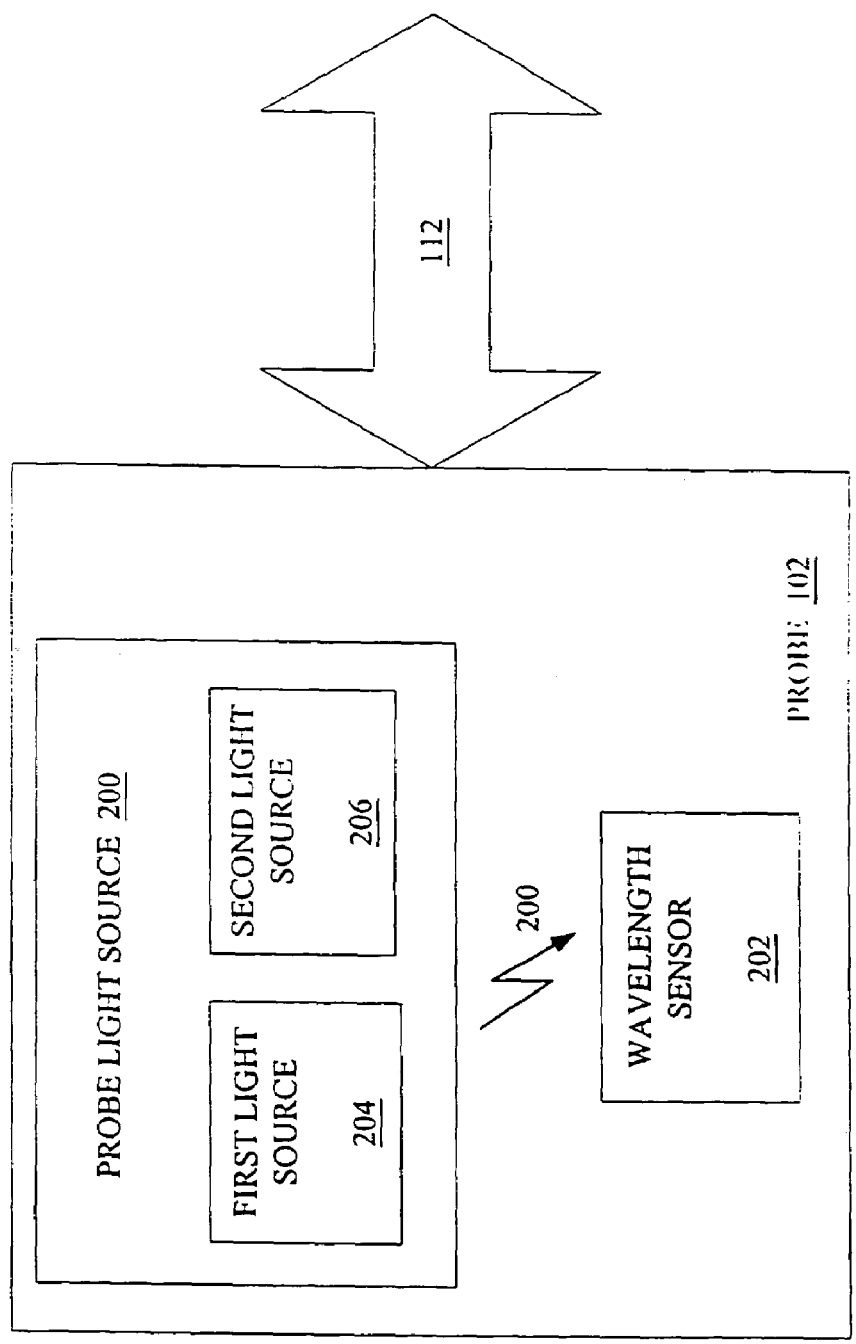
FIG. 2 illustrates a block diagram of an example implementation of the probe block of the SCSS shown FIG. 1.

FIG. 2 shows an example implementation of probe 102. Probe 102 may include a probe light source 200 and wavelength sensor 202. Probe light source 200 may include a first light source 204 and second light source 206. First light source 204 and second light source 206 may be implemented utilizing light-emitting diodes (LEDs). As an example implmentation in oximeter application, first light source 204 may be an LED emitting light radiation at a wavelength of approximately 660 nm and second light source 206 may be an LED emitting light radiation at a wavelength of approximately 880 nm. Wavelength sensor 202 may be implemented utilizing a double diffusion photodiode. It is appreciated by those of skill in the art that probe light source 200 may also include multiple light sources in the order of three or more.

Figure 3:
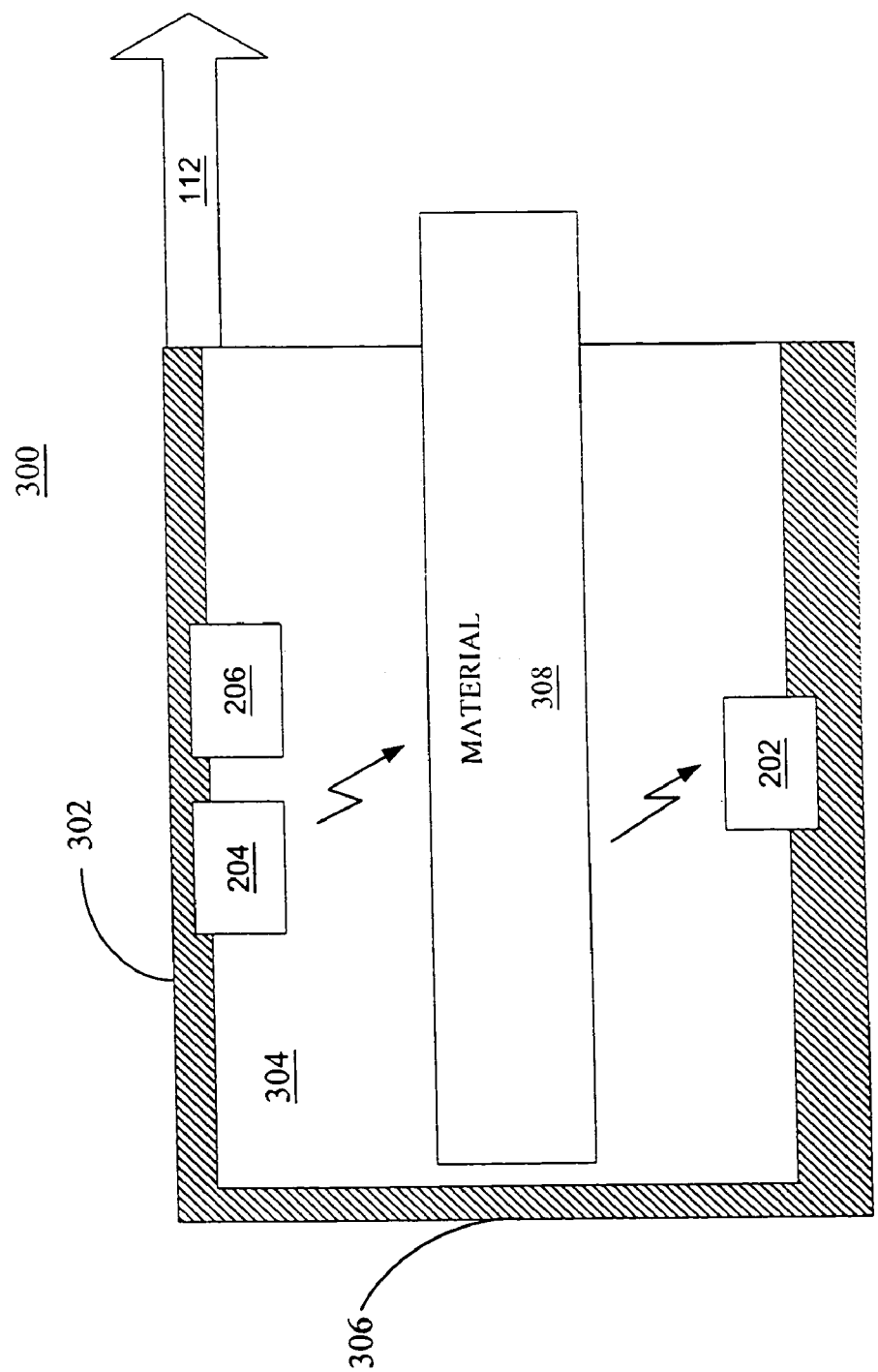
FIG. 3 illustrates a cross-sectional view of an example implementation of the probe shown in FIG. 2.

In FIG. 3, a cross-sectional view of an example implementation of the probe 300 is shown. In this example, probe 300 may be a medical device such as a transmissive blood oxygen saturation and pulse rate sensor. However, it would be appreciated by one skilled in the art that probe 300 may also be a reflective sensor. Additionally, probe 300 may also be utilized for measuring other blood constituents including, but not limited to, oxyhemoglobin, bilirubin, carboxy-hemoglobin, and glucose. Probe 300 may include a rigid casing 302 having a cavity 304 and casing butt 306, first light source 204, second light source 206 and wavelength sensor 202. Probe 300 is connected to calibration circuit 104, FIG. 1, via signal path 112. A material 308, FIG. 3, such as a finger may be inserted into the cavity 304.

As an example, first light source 204 and second light source 206 may be two LED emitters that produce light radiation at a wavelength of approximately 660 nm and 880 nm, respectively. Wavelength sensor 202 is supported within the rigid casing 302 opposite first light source 204 and second light source 206. First light source 204 and second light source 206 and wavelength sensor 202 may be in signal communication with a control cable (not shown). The control cable is in signal communication with an oximeter (not shown) via signal path 112. The oximeter determines the oxygen saturation of the blood in the material 308 (in this example a finger) by measuring and processing the amount of incident light radiation reaching wavelength sensor 202 from a pulse of light radiation from first light source 204.

In operation, the SCSS 100, FIG. 1, performs a self-calibration procedure prior to measuring any of the properties of the material 308, FIG. 3. This self-calibration procedure includes emitting a pulse of light radiation from the first light source 204 that is received as incident light radiation by wavelength sensor 202 prior to inserting material 308 into the cavity 304. The oximeter utilizes the measured incident light radiation received by wavelength sensor 202 to determine the operating wavelength of the first light source 204. Once the operating wavelength of the first light source 203 is known, the SCSS 100, FIG. 1, is utilized in combination with the oximeter to accurately determine blood oxygen saturation of the material 308.

The self-calibration procedure is beneficial because it is appreciated by those skilled in the art that light radiation output by first light source 204 of 660 nm in this example implementation is in the red spectral region. It is the absorption of this red light radiation that the oximeter utilizes to determine the oxygen saturation of the blood. As such, a relatively small variation in operating wavelength may results in inaccurate readings at the oximeter. As an example, without the self-calibration procedure, if the light radiation output by first light source 204 varied in excess of ±2 nm from an operating wavelength required by the oximeter, the results would be inaccurate.

Figure 4A:
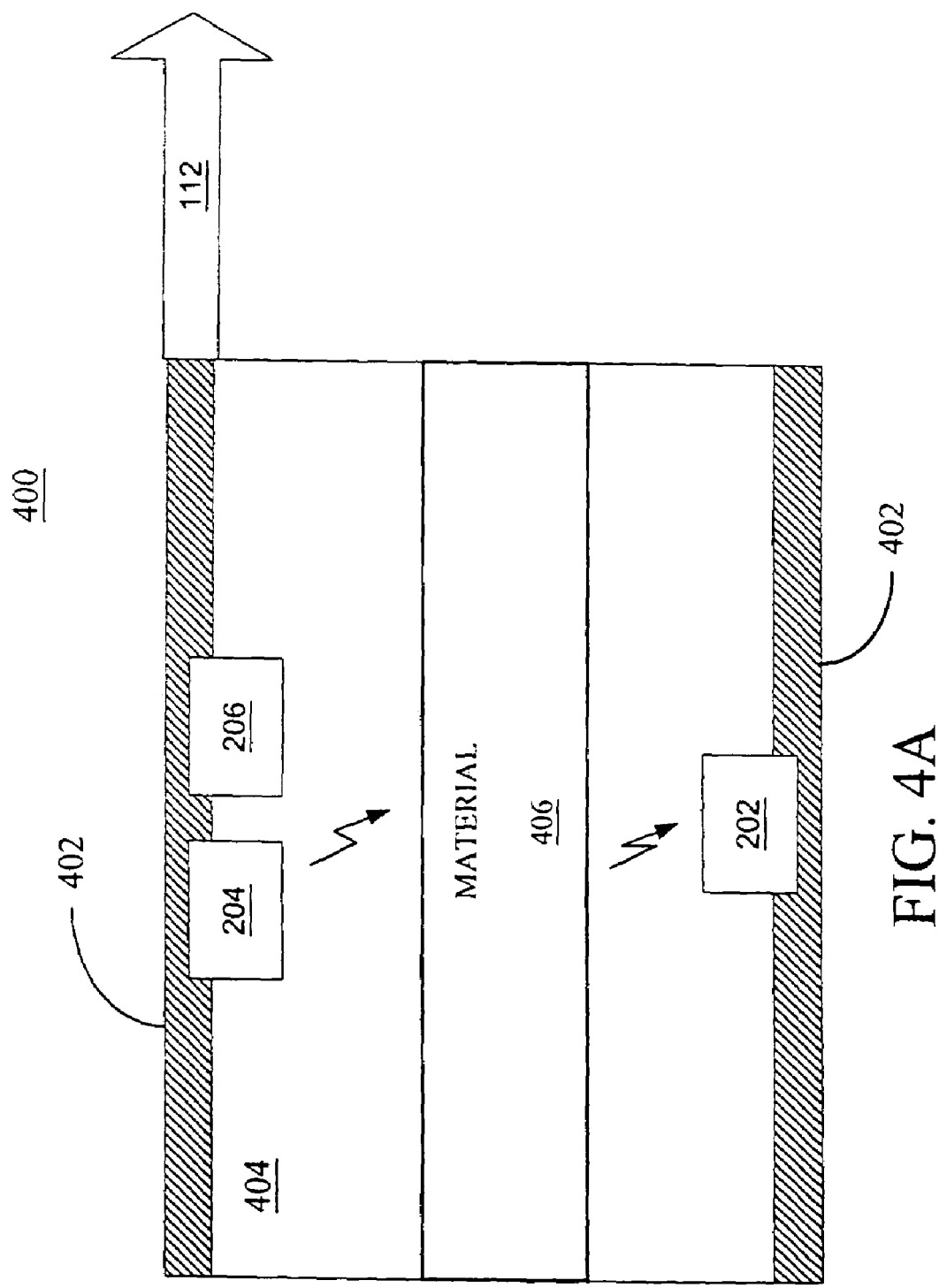
FIG. 4A illustrates a cross-sectional view of another example implementation of the probe shown in FIG. 2.

FIG. 4A illustrates a cross-sectional view of another example implementation of probe 400. In this example, probe 400 may include a rigid or flexible casing 402 having a cavity 404, first light source 204, second light source 206 and wavelength sensor 202. Similar to the previous example implementation, probe 400 is connected to calibration circuit 104, FIG. 1, via signal path 112, however, probe 400, FIG. 4A, does not have a cavity butt. A material 406 may be inserted into the cavity 404.

Similar to the previous example, first light source 204 and second light source 206 may be two LED emitters that produce light radiation at different wavelengths. Wavelength sensor 202 is supported within the rigid casing 402 opposite first light source 204 and second light source 206. First light source 204 and second light source 206 and wavelength sensor 202 may be in signal communication with a control cable (not shown). The control cable is in signal communication with a measuring device (not shown) via signal path 112. The measuring device determines the properties in the material 406 by measuring and processing the amount of incident light radiation reaching wavelength sensor 202 from a pulse of light radiation from first light source 204.

As an industrial example, the material 406 may be a fluid, liquid or solid material that exhibits optical transmissive characteristics that may be measured and utilized to determine the properties of the material. An example implementation would include measuring the properties of the material for process or quality control purposes.

Again in operation, the SCSS 100, FIG. 1, performs a self-calibration procedure prior to measuring any of the properties of the material 406, FIG. 4A. This self-calibration procedure includes emitting a pulse of light radiation from the first light source 204 that is received as incident light radiation by wavelength sensor 202 prior to inserting material 406 into the cavity 404. The measuring device utilizes the measured incident light radiation received by wavelength sensor 202 to determine the operating wavelength of the first light source 204. Once the operating wavelength of the first light source 204 is known, the SCSS 100, FIG. 1, is utilized in combination with the measuring device to accurately determine the properties of the material 406.

FIG. 4B illustrates a cross-sectional view of an example reflective implementation of probe 408. In this example, probe 408 may include a rigid or flexible casing 410 having a cavity 412, first light source 204, second light source 206 and wavelength sensor 202. Similar to the previous example implementation, probe 408 is connected to calibration circuit 104, FIG. 1, via signal path 112, however, probe 408, FIG. 4B, does not have a cavity butt. A material 412 may be inserted into the cavity 412.

Similar to the previous example, first light source 204 and second light source 206 may be two LED emitters that produce light radiation at different wavelengths. However, in this example, wavelength sensor 202 is supported within the rigid casing 410 adjacent to first light source 204 and second light source 206. First light source 204 and second light source 206 and wavelength sensor 202 may be in signal communication with a control cable (not shown). The control cable is in signal communication with a measuring device (not shown) via signal path 112. The measuring device determines the properties in the material 412 by measuring and processing the amount of incident light radiation reflected by material 412 and reaching wavelength sensor 202 from a pulse of light radiation from first light source 204.

Again, as an industrial example, the material 412 may be a fluid, liquid or solid material that exhibits optical transmissive characteristics that may be measured and utilized to determine the properties of the material. An example implementation would include measuring the properties of the material for process or quality control purposes.

Again in operation, the SCSS 100, FIG. 1, performs a self-calibration procedure prior to measuring any of the properties of the material 412, FIG. 4B. This self-calibration procedure includes emitting a pulse of light radiation from the first light source 204 that is reflected by flexible casing 410 and later received as incident light radiation by wavelength sensor 202 prior to inserting material 412 into the cavity 410. The measuring device utilizes the measured incident light radiation received by wavelength sensor 202 to determine the operating wavelength of the first light source 204. Once the operating wavelength of the first light source 204 is known, the SCSS 100, FIG. 1, is utilized in combination with the measuring device to accurately determine the properties of the material 412.

It is appreciated by of skill in the art that it is possible to generate signals from the wavelength sensor 202, FIG. 2 during operation of the light sources 204 and 206 through the medium (i.e., material 308, FIG. 3, 406, FIG. 4A, and/or 414, FIG. 4B) being inspected. It is also possible to generate the same signals using light reflected off the medium. Therefore, it is not necessary to couple the light sources 204, FIG. 2 and 206 directly to the wavelength sensor 202 as long as the medium either transmits or reflects enough light to generate processable signals from the wavelength sensor 202.

Figure 5:
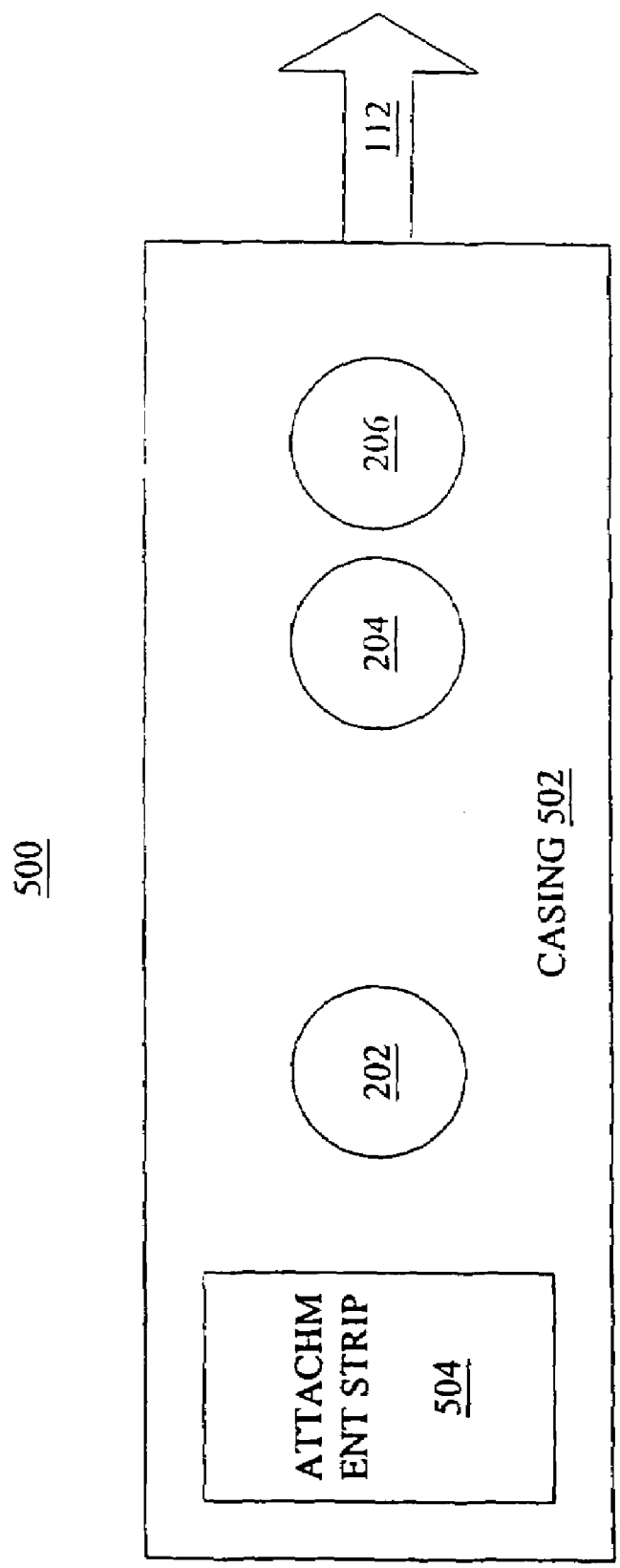
FIG. 5 is a top view of an example implementation of the probe shown in FIG. 4.

In FIG. 5, a top view of an example medical implementation of probe 500 having a flexible casing (i.e., flexible strip) 502 is shown. Probe 500 may include first light source 204, second light source 206 and wavelength sensor 202. In this example implementation, probe 500 is a blood oxygen saturation and pulse rate sensor that utilizes the flexible strip 502 to attach to a material, such as a body part (not shown). The probe 500 is connected to an oximeter (not shown) via signal path 112. The flexible strip 502 may be wrapped around the body part and affixed to itself via an attachment strip (such as an adhesive strip) 504. Example body parts would include a finger, toe, ear-lobe, arm, leg or other similar parts.

As an example, first light source 204 and second light source 206 may be two LED emitters that produce light radiation at a wavelength of approximately 660 nm and 880 nm, respectively. Wavelength sensor 202 is supported within the flexible strip 502 and placed opposite first light source 204 and second light source 206 when the flexible strip 502 is wrapped around a body part. First light source 204 and second light source 206 and wavelength sensor 202 may be in signal communication with a control cable (not shown). The control cable is in signal communication with an oximeter (not shown) via signal path 112. The oximeter determines the oxygen saturation of the blood in the body part by measuring and processing the amount of incident light radiation reaching wavelength sensor 202 from a pulse of light radiation from first light source 204.

Figure 6:
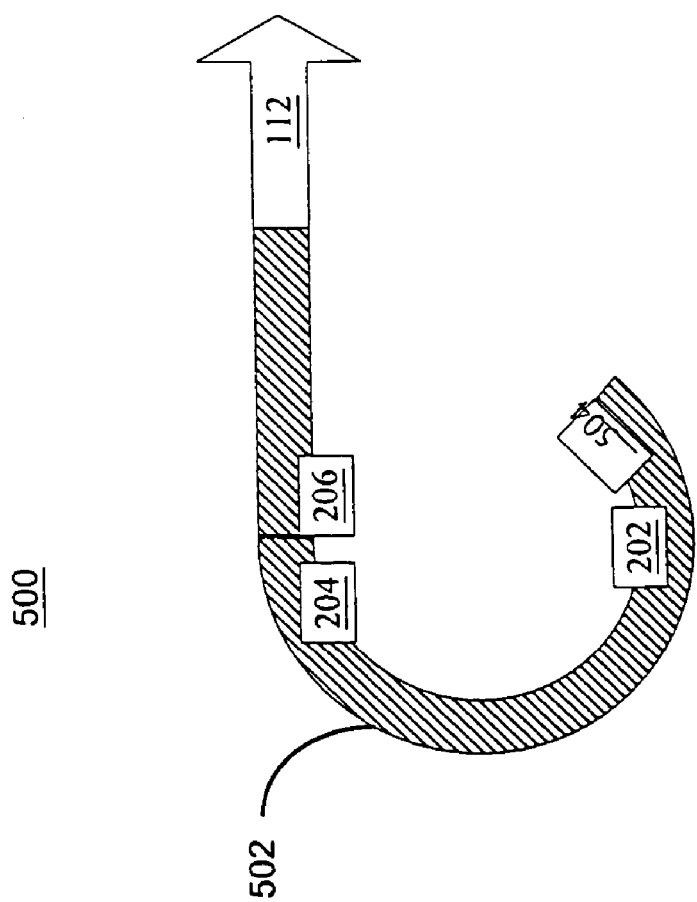
FIG. 6 is a cross-sectional view of the probe implementation of FIG. 5.

As before, in operation, the SCSS 100, FIG. 1, performs a self-calibration procedure prior to measuring any of the properties of the body part. This self-calibration procedure includes, prior to wrapping flexible strip 502 around the body part, bending the flexible strip 502 so that the first light source 204 and second light source 206 are opposite in special orientation to wavelength sensor 202 and then emitting a pulse of light radiation from the first light source 204 that is received as incident light radiation by wavelength sensor 202. The oximeter utilizes the measured incident light radiation received by wavelength sensor 202 to determine the operating wavelength of the first light source 204. Once the operating wavelength of the first light source 204 is known, placed around a body part and the wavelength sensor 202 measures the incident light radiation emitted by the first light source 204 and passing through the blood flowing within the body part. The SCSS 100, FIG. 1, is then utilized in combination with the oximeter to accurately determine blood oxygen saturation of the body part. In FIG. 6, a cross-sectional view of the probe 500 is shown in a wrap type position.

Figure 7:
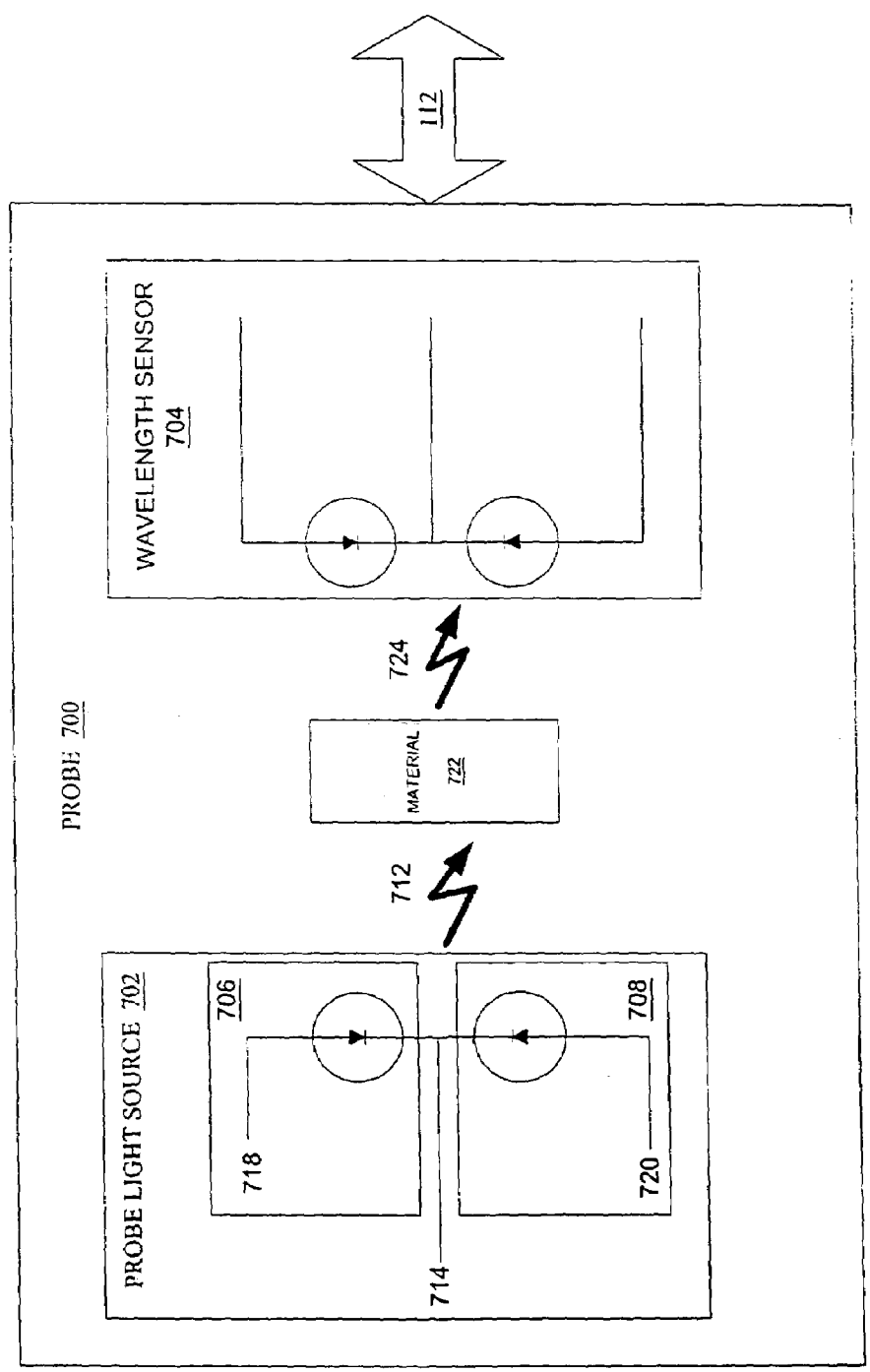
FIG. 7 illustrates an example implementation of the probe block shown in FIG. 2 utilizing photodiodes.

In FIG. 7, an example implementation of the probe 700 is shown utilizing photodiodes. Similar to FIG. 2, Probe 700, FIG. 7, includes probe light source 702 and wavelength sensor 704. Probe light source 702 includes first light source 706 and second light source 708. First light source 706 may include LED 710 and second light source may include LED 712. Wavelength sensor 704 is a double diffusion photodiode.

As an example of operation, LED 710 and LED 712 may have their cathodes grounded in common at signal path 714 and may emit light radiation 716 at wavelengths 660 nm and 880 nm, respectively, when a voltage is applied at anodes 718 and 720, respectively. The emitted light radiation 716 is incident on material 722. A part of the emitted light radiation 716 is transmitted through material 722 and is received as incident light radiation 724 by wavelength sensor 704. As before, in order to properly measure the properties of the material 722 from the received incident light radiation 724, the SCSS 100, FIG. 1 performs a self-calibration procedure.

The SCSS 100, FIG. 1, performs a self-calibration procedure prior to measuring any of the properties of the material 722. This self-calibration procedure includes emitting a pulse of light radiation 716 from LED 710 that is received as incident light radiation 724 by wavelength sensor 704 prior to inserting material 722 between the probe light source 702 and wavelength sensor 704. The oximeter utilizes the measured incident light radiation 724 received by wavelength sensor 704 to determine the operating wavelength of LED 710. Once the operating wavelength of LED 710 is known, the SCSS 100, FIG. 1, is utilized in combination with the oximeter to accurately determine blood oxygen saturation of the material 722.

Figure 8:
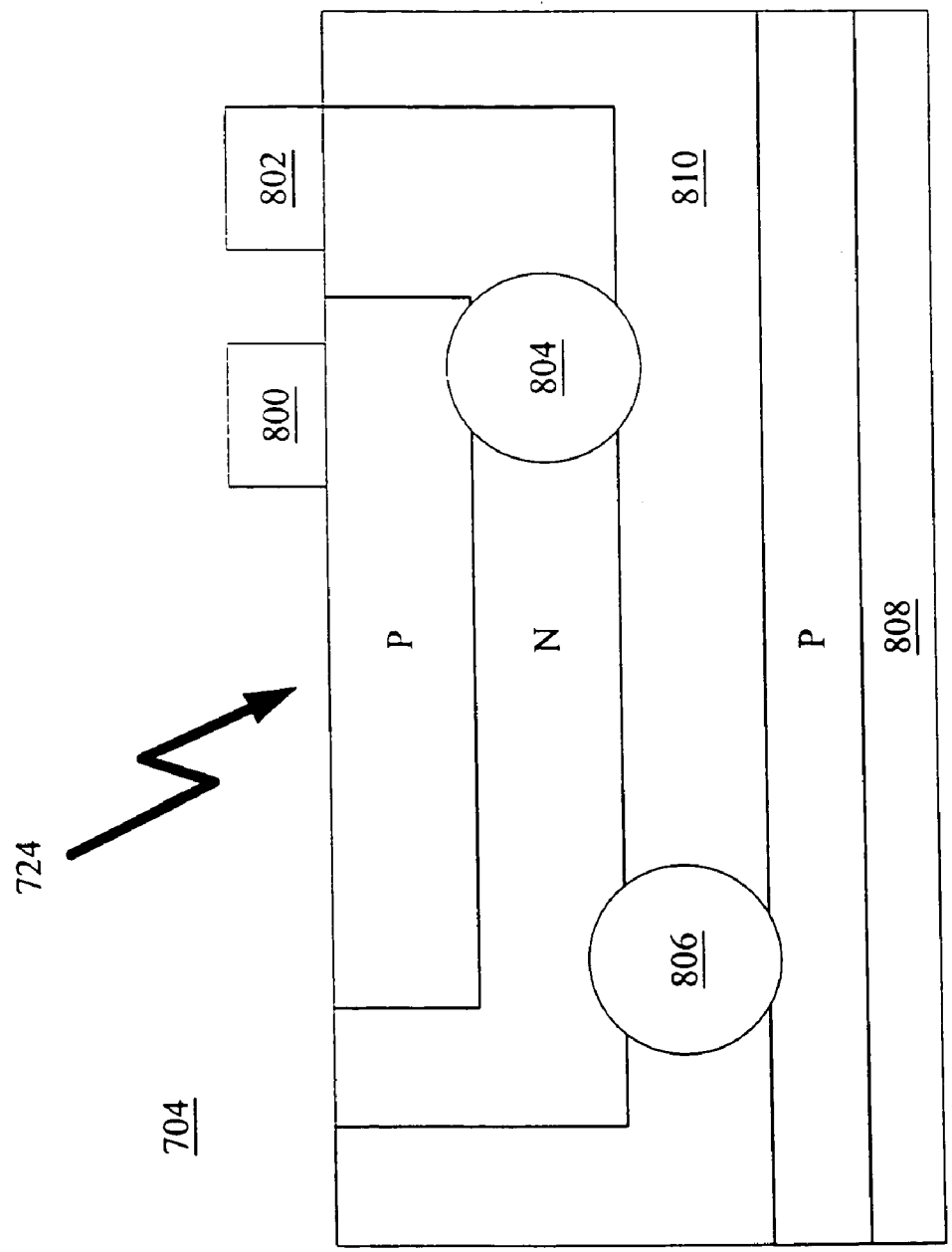
FIG. 8 illustrates a cross-sectional view of an example implementation of the wavelength sensor block shown in FIG. 7 utilizing a double diffusion photodiode.

FIG. 8 illustrates a cross-sectional view of the wavelength sensor 704 receiving incident light radiation 724 utilizing a double diffusion photodiode (also known as a double junction photodiode). Photodiodes with double diffusion are typically utilized to accurately measure the centroid wavelength of light sources such as LEDs 710 and 712. Double diffusion photodiodes are processed with two junctions, one on the top surface and one on the back surface of a semiconductor photodiode (such as a Si-photodiode), each junction typically exhibits a different and well-defined spectral response. As result, by measuring the quotient of signals generated by the two junctions, the centroid wavelength of any given monochromatic light source may be determined.

The wavelength sensor 704 has two p-n junctions constructed vertically on a common silicon substrate. The wavelength sensor 704 includes a first anode 800, common cathode 802, first diode 804 (also known as an upper diode), second diode 806 (also known as a lower diode), second anode 808, and a thin active region 810. The first anode 800 is positioned on the top surface above the common cathode 802 forming the first diode 804. The thickness of the first diode 804 is chosen so that the energy of the shortest wavelength being measured from the incident light radiation 724 is absorbed entirely therein. The second diode 806 is formed between the common cathode 802 and the second anode 808 that placed on the bottom surface with the thin active region 810 between the common cathode 802 and the second anode 808. The thickness of the thin active region 810 is selected to allow for absorption of substantially all of the longest measured wavelength of incident light radiation 724.

Figure 9:
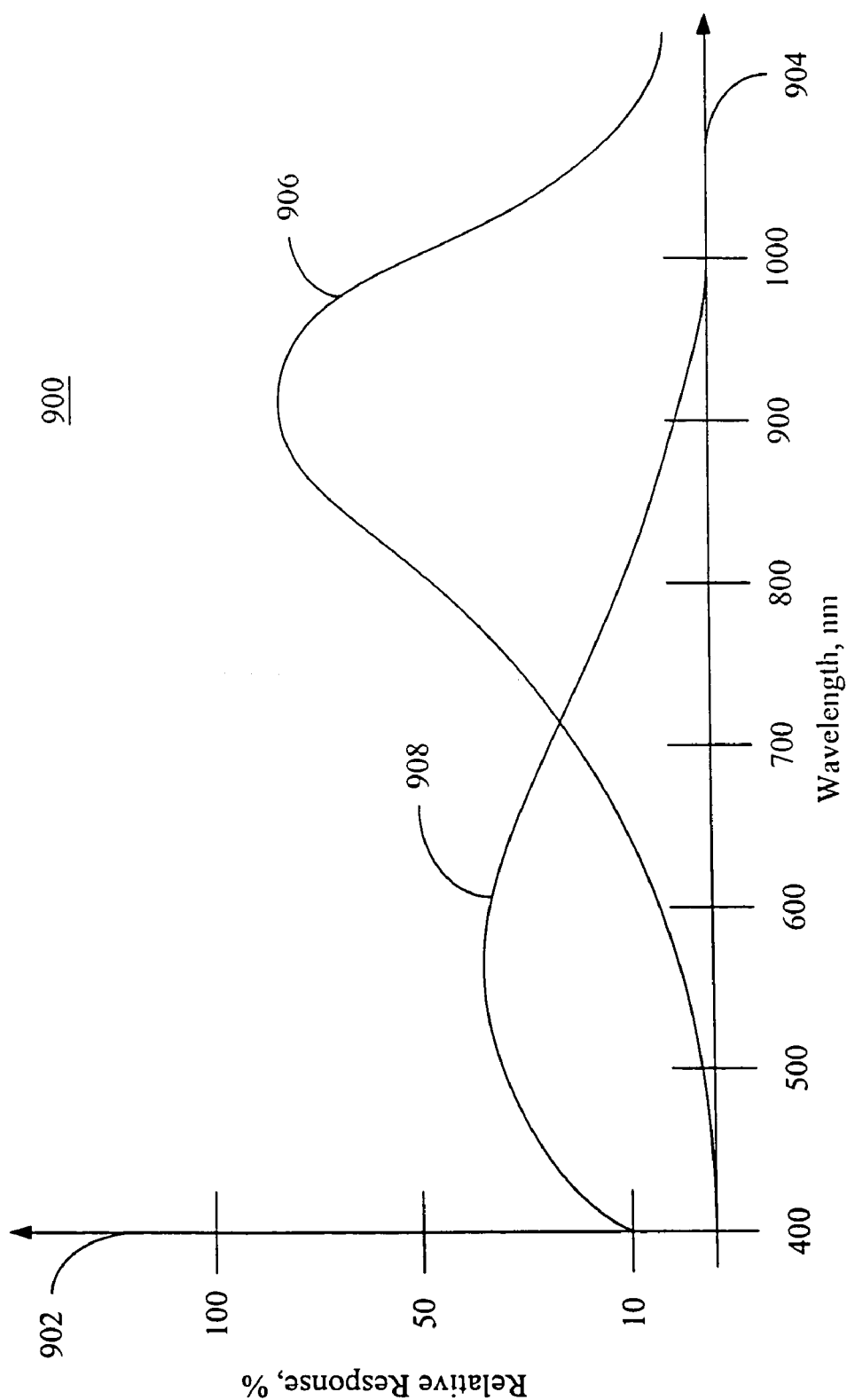
FIG. 9 is a graph of the response curve of the wavelength sensor shown in FIG. 8.

FIG. 9 illustrates a typical plot 900 of the spectral response of the wavelength sensor 704, FIG. 8. The plot 900, FIG. 9, has a vertical axes 902 representing relative response, in percentage, of the wavelength sensor 704, FIG. 8, and a horizontal axis 904, FIG. 9, representing the wavelength of the incident light radiation 724, FIG. 8. The plot 900, FIG. 9, shows two response curves 906 and 908 representing the relative response versus wavelength for the first diode 804, FIG. 8, and the second diode 806, respectively.

As an example of operation of the wavelength sensor 704, the first diode 804 may have an enhanced blue response and the second diode 806 may have an enhanced red response. In this example, the absorbed radiation of the incident light radiation 724 between the red and blue responses (such as between 450 and 900 nm) generates two photocurrent signals proportional to the wavelength of the incident light radiation 724. The quotient of these photocurrent signals is independent of the light level up to the saturation point of the wavelength sensor 704. Utilizing this example, the wavelength of either monochromatic incident light radiation 724 or the spectral density peak of polychromatic incident light radiation 724 may be determined. An example of the wavelength sensor 704 may be a PSS WS-7.56 wavelength sensor produced by Pacific Silicon Sensor, Inc. of Westlake Village, Calif.

Figure 10:
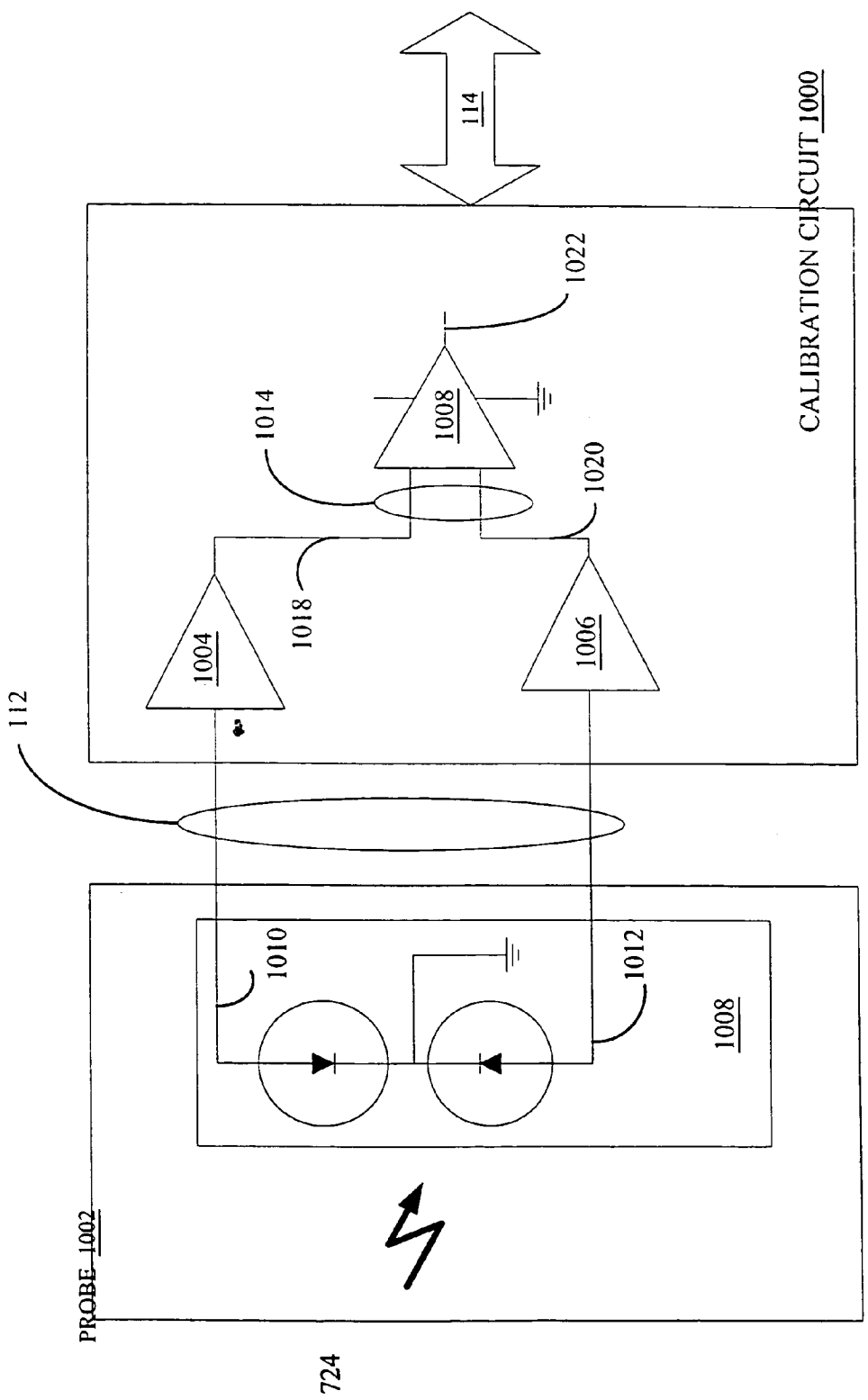
FIG. 10 is schematic diagram depicting an exemplary implementation of the calibration circuit block shown in FIG. 1.

In FIG. 10, a schematic diagram depicting an exemplary implementation of the calibration circuit 1000 is shown. The calibration circuit 1000 is in signal communication with the probe 1002 and controller 106, FIG. 1, via signal paths 112 and 114, respectively. The calibration circuit 1000 may include a pair of amplifiers 1004 and 1006 (such as log amplifiers) in signal communication with first anode 800, FIG. 8 and second anode 808 of wavelength sensor 1008, FIG. 10, and a differential amplifier 1010, via signal paths 1010, 1012 and 1014, respectively. The differential amplifier 1008 is in signal communication with the controller 106, FIG. 1, via signal path 112.

In operation, the wavelength sensor 1004 produces two photocurrent signals from the two junctions (i.e., photodiodes 804 and 806) in the double diffusion photodiode. Each junction in the wavelength sensor 1004 exhibits a different and well-defined spectral response, which is know to the controller 106, FIG. 1, and the magnitude of these two resulting photocurrent signals are proportional to the wavelength of the measured incident light radiation 724, which corresponds to one of the light sources (either 204 or 206, FIG. 2) in probe 1002, FIG. 10. The photocurrent signals are amplified by amplifiers 1004 and 1006 via signal paths 1010 and 1012, respectively, and input into the differential amplifier 1008 via signal path 1018 and 1020. If the amplified photocurrent signals 1018 and 1020 are approximately equal the corresponding differential output signal 1022 of the differential amplifier 1008 is almost equal to zero. Once the differential output signal 1022 is almost equal to zero the wavelength of the incident light radiation is determined and the SCSS 100, FIG. 1, is calibrated.

When the amplified photocurrent signals 1018 and 1020 are not approximately equal the corresponding differential output signal 1022 will vary according to the difference in magnitude value between the amplified photocurrent signals 1018 and 1020. The differential output signal 1022 is the utilized as a reference by the controller 106, FIG. 1. The controller 106 determines the wavelength of the incident light radiation 724 by knowing the spectral response of the photodiodes 804 and 806, FIG. 8. The controller 106 either determines the wavelength of the incident light radiation 724 utilizing software 108 or other hardware (not shown) located in the SCSS 100. The software 108 may include logic that allows the controller 106 to calculate the wavelength values in real-time from the measure values received from the wavelength sensor 1004.

Alternatively, the controller 106 may determine the wavelength of the incident light radiation 724 utilizing the lookup ("LUT") table 110. The LUT 110 may be resident in memory (not shown) resident either internally or externally to the controller 106. The LUT 110 includes a tabulation of known spectral response in voltage versus wavelength for each photodiode 804 and 806, FIG. 8. Once the controller 106 measures the differential output signal 1022, FIG. 10, the software 108, FIG. 1, compares the value of the differential output signal 1022, FIG. 10, against values stored in the LUT 110, FIG. 1, and then retrieves a corresponding wavelength value. The controller 106 then utilizes the retrieved wavelength wave to self-calibrate the SCSS 100.

Besides self-calibration, the SCSS 100 is also capable of temperature compensating for variation in the wavelength of the incident light radiation 724 due to temperature variations. The SCSS 100 may compensate for temperature variations by the same process utilized to self-calibrate.

Figure 11:
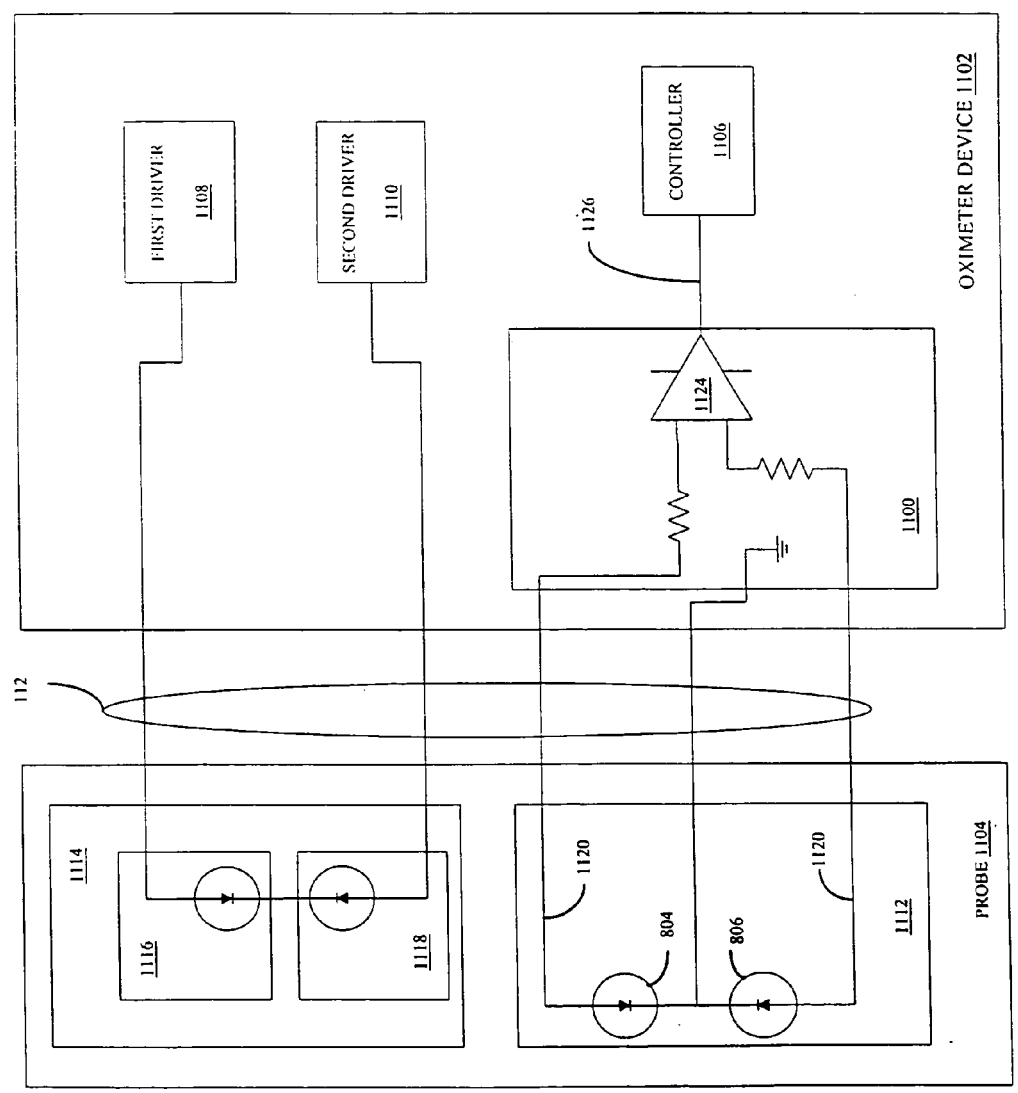
FIG. 11 is schematic diagram depicting another exemplary implementation of the calibration circuit block shown in FIG. 1.

FIG. 11 is another exemplary implementation of the SCSS 100, FIG. 1, with the calibration circuit 1100, FIG. 11, in an oximeter device 1102. The oximeter device 1102 is in signal communication with probe 1104, via signal path 112, and includes calibration circuit 1100, controller 1106, first driver 1108 and second driver 1110. The probe 1104 includes wavelength sensor 1112 and probe light source 1114 having first light source 1116 and second light source 1118.

In operation, the first driver 1108 drives the first light source 1116 and the second driver 1110 drives the second light source 1118. First light source 1116 and the second light source 1118 may individually produce light radiation which is incident of the wavelength sensor 1112. The wavelength sensor 1112 produces two photocurrent signals from the two junctions (i.e., photodiodes 804 and 806) in the double diffusion photodiode. Again, each junction in the wavelength sensor 1112 exhibits a different and well-defined spectral response, which is know to the controller 1106 and the magnitude of these two resulting photocurrent signals are proportional to the wavelength of the measured incident light radiation, which corresponds to one of the light sources (either 1116 or 1118) in probe 1104. The photocurrent signals 1120 and 1122 processed and input into the differential amplifier 1224. If the photocurrent signals 1120 and 1122 are approximately equal the corresponding differential output signal 1126 of the differential amplifier 1124 is almost equal to zero. Once the differential output signal 1126 is almost equal to zero the wavelength of the incident light radiation is determined and the SCSS 100, FIG. 1, is calibrated.

When the photocurrent signals 1120 and 1122 are not approximately equal the corresponding differential output signal 1126 will vary according to the difference in magnitude value between the photocurrent signals 1120 and 1122. The differential output signal 1126 is the utilized as a reference by the controller 1106. The controller 1106 determines the wavelength of the incident light radiation by knowing the spectral response of the photodiodes 804 and 806. The controller 1106 either determines the wavelength of the incident light radiation utilizing software 108, FIG. 1, or other hardware (not shown) located in the SCSS 100. The software 108 may include logic that allows the controller 1106, FIG. 11, to calculate the wavelength values in real-time from the measure values received from the wavelength sensor 1112.

Alternatively, the controller 1106 may determine the wavelength of the incident light radiation utilizing the lookup LUT 110, FIG. 1. The LUT 110 may be resident in memory (not shown) resident either internally or externally to the controller 1106, FIG. 11. The LUT 110, FIG. 1, includes the tabulation of known spectral response in voltage versus wavelength for each photodiode 804 and 806. Once the controller 1106 measures the differential output signal 1126, FIG. 11, the software 108, FIG. 1, compares the value of the differential output signal 1126, FIG. 11, against values stored in the LUT 110, FIG. 1, and then retrieves a corresponding wavelength value. The controller 1106, FIG. 11, then utilizes the retrieved wavelength wave to self-calibrate the SCSS 100, FIG. 1.

Figure 12:
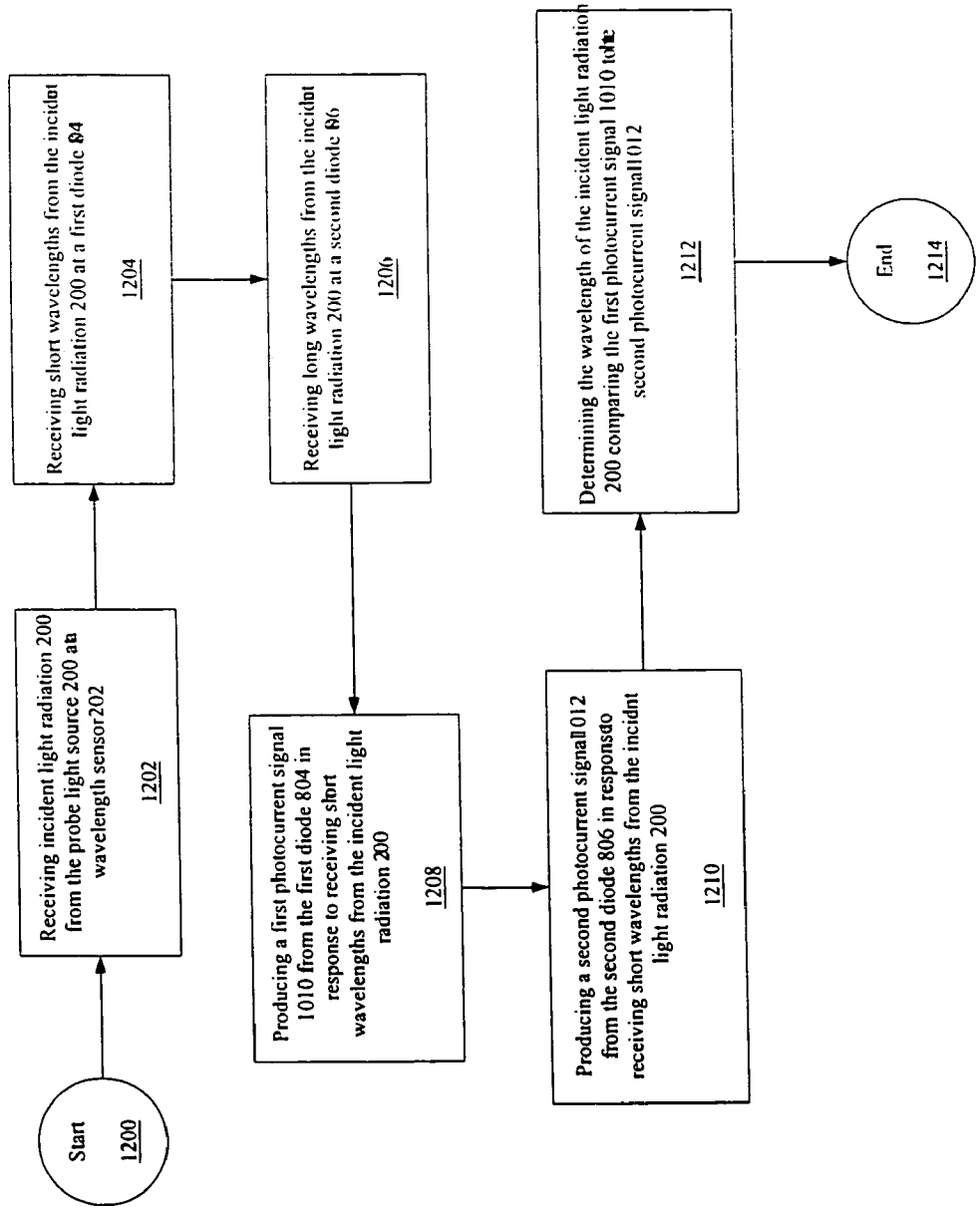
FIG. 12 is a flow chart illustrating the process performed by the SCSS shown in FIG. 1.

FIG. 12 illustrates the process performed by the SCSS 100, FIG. 1. The process begins in step 1200, FIG. 12. In step 1202, the wavelength sensor 202, FIG. 2, receives incident light radiation 200 from the probe light source 200. Within the wavelength sensor 202, the first diode 804, FIG. 8, receives short wavelengths from the incident light radiation 200, in step 1204, FIG. 12, and the second diode 806, FIG. 8, receives long wavelengths from the incident light radiation 200 in step 1206, FIG. 12. In step 1208, the first diode 804 produces a first photocurrent signal 1010, FIG. 10, in response to receiving short wavelengths from the incident light radiation 200 and the second diode 806 produces a second photocurrent signal 1012, FIG. 10, in response to receiving short wavelengths from the incident light radiation 200 in step 1210, FIG. 12. Finally, in step 1212, the calibration circuit 104 and/or controller 106, FIG. 1, determine the wavelength of the incident light radiation 200 by comparing the first photocurrent signal 1010 to the second photocurrent signal 1012. The process then ends in step 1214.

The SCSS 100 may be selectively implemented in software, hardware, or a combination of hardware and software. For example, the elements of the SCSS 100 may be implemented in software 108 stored in a memory (not shown) located in a controller 106. The controller 106 may be in signal communication with a DSP or ASIC chip via communication link 112 (which may selectively be a system bus). The software 108 configures and drives the DSP or ASIC chip and performs the steps illustrated in FIG. 12.

The software 108 comprises an ordered listing of executable instructions for implementing logical functions. The software 108 may be embodied in any computer-readable medium for use by or in connection with an instruction execution system, apparatus, or device, such as a computer-based system, processor-containing system, or other system that may selectively fetch the instructions from the instruction execution system, apparatus, or device and execute the instructions. In the context of this document, a "computer-readable medium" is any means that may contain, store, communicate, propagate, or transport the program for use by or in connection with the instruction execution system, apparatus, or device. The computer readable medium may be for example, but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a RAM (electronic), a read-only memory (ROM) (electronic), an erasable programmable read-only memory (EPROM or Flash memory) (electronic), an optical fiber (optical), and a portable compact disc read-only memory (CDROM) (optical). Note that the computer-readable medium may even be paper or another suitable medium upon which the program is printed, as the program can be electronically captured, via for instance optical scanning of the paper or other medium, then compiled, interpreted or otherwise processed in a suitable manner if necessary, and then stored in a computer memory.

While various implementations of the application have been described, it will be apparent to those of ordinary skill in the art that many more embodiments and implementations are possible that are within the scope of the invention. Accordingly, the invention is not to be restricted except in light of the attached claims and their equivalents.

What is claimed is:

1. A sensor system comprising:
   a probe comprising a light source and a sensor, the sensor having a probe calibration output and a calibrated probe output, wherein the probe outputs are responsive to incident light radiation received from the light source to produce signals proportional to an amplitude and a centroid wavelength of the incident light, and the probe calibration output is generated continuously while taking a physiological measurement;
   a calibration circuit in signal communication with the probe and comprising an electronic calibration output responsive to the probe calibration output, and a calibrated electronic output responsive to the calibrated probe output;
   a controller in signal communication with the calibration circuit and comprising a lookup table having a wavelength value output responsive to the electronic calibration output and the calibrated electronic output, wherein the wavelength value output is determined in real-time and is then used to correct physiological data derived from the signal proportional to the amplitude of the incident light; and,
   a measuring device comprising an output generated in response to the wavelength value output.

2. The sensor system of claim 1, wherein the physiological measurement and the output of the measuring device is oxygen saturation within blood.

3. The sensor system of claim 1, further comprising software that operates on the controller.

4. The sensor system of claim 3, the software comprising instructions for compensating for wavelength variation of the incident light radiation caused by changes in temperature.

5. The sensor system of claim 1, wherein the incident light radiation is coherent.

6. A sensor system comprising:
   a probe comprising a light source and a sensor, the sensor having a probe calibration output and a calibrated probe output, wherein the probe outputs are responsive to incident light radiation received from the light source to produce signals proportional to an amplitude and a centroid wavelength of the incident light, and the probe calibration output is generated continuously while taking a physiological measurement;
   a calibration circuit in signal communication with the probe and comprising an electronic calibration output responsive to the probe calibration output, and a calibrated electronic output responsive to the calibrated probe output;
   a controller in signal communication with the calibration circuit and comprising a software-based logic responsive to the electronic calibration output and the calibrated electronic output to produce a wavelength value output is then used to correct physiological data derived from the signal proportional to the amplitude of the incident light; and,
   a measuring device comprising an output generated in response to the wavelength value output.

7. The sensor system of claim 6, wherein the physiological measurement and the output of the measuring device are oxygen saturation within blood, cardiac output, blood pressure, or vital signs.

8. The sensor system of claim 6, further comprising software that operates on the controller.

9. The sensor system of claim 8, the software comprising instructions for compensating for wavelength variation of the incident light radiation caused by changes in temperature.

10. The sensor system of claim 6, wherein the incident light radiation is coherent.

11. A sensor system comprising:
    a probe comprising a light source and a sensor, the sensor having a probe calibration output and a calibrated probe output, wherein the probe outputs are responsive to incident light radiation received from the light source to produce signals proportional to an amplitude and a centroid wavelength of the incident light, and the probe calibration output is generated continuously while taking a physiological measurement;
    a calibration circuit in signal communication with the probe and comprising an electronic calibration output responsive to the probe calibration output, and a calibrated electronic output responsive to the calibrated probe output;
    a controller in signal communication with the calibration circuit and comprising logic responsive to the electronic calibration output to provide an output to adjust light source temperature and to produce a wavelength value output that is determined in real-time and is then used to correct physiological data derived from the signal proportional to the amplitude of the incident light; and,
    a measuring device comprising an output generated in response to the wavelength value output.

12. The sensor system of claim 11, wherein the physiological measurement and the output of the measuring device are oxygen saturation within blood, cardiac output, blood pressure, or vital signs.

13. The sensor system of claim 11, further comprising software that operates on the controller.

14. The sensor system of claim 13, the software comprising instructions for compensating for wavelength variation of the incident light radiation caused by changes in temperature.

15. The sensor system of claim 11, wherein the incident light radiation is coherent.

16. A sensor system comprising:
    a probe comprising a light source and a sensor, the sensor having a probe calibration output and a calibrated probe output, wherein the probe outputs are responsive to incident light radiation received from the light source to produce signals proportional to an amplitude and a centroid wavelength of the incident light, and the probe calibration output is generated prior to taking a physiological measurement;
    a calibration circuit in signal communication with the probe and comprising an electronic calibration output responsive to the probe calibration output, and a calibrated electronic output responsive to the calibrated probe output;
    a controller in signal communication with the calibration circuit and comprising logic responsive to the electronic calibration output and the calibrated electronic output to produce a wavelength value output that is used to determine, in real-time, the physiological measurement, and is then used to correct physiological data derived from the signal proportional to the amplitude of the incident light.

17. The sensor system of claim 16, wherein the physiological measurement is oxygen saturation within blood, cardiac output, blood pressure, or vital signs.

18. The sensor system of claim 16, further comprising software that operates on the controller.

19. The sensor system of claim 18, the software comprising instructions for compensating for wavelength variation of the incident light radiation caused by changes in temperature.

20. The sensor system of claim 16, wherein the incident light radiation is coherent.

* * * * *

UNITED STATES PATENT AND TRADEMARK OFFICE
CERTIFICATE OF CORRECTION

| | | |
|---|---|---|
| PATENT NO. | : 7,124,048 B2 | Page 1 of 1 |
| APPLICATION NO. | : 11/007656 | |
| DATED | : October 17, 2006 | |
| INVENTOR(S) | : Dietiker | |

It is certified that error appears in the above-identified patent and that said Letters Patent is hereby corrected as shown below:

On the Title page of the patent, line 60, item 60, the line should read --Provisonal application No. 60/225,021, filed on August 11, 2000-- and not August 11, 2001.

Signed and Sealed this

Ninth Day of January, 2007

JON W. DUDAS
*Director of the United States Patent and Trademark Office*